US005392778A

United States Patent [19]
Horzewski

[11] Patent Number: 5,392,778
[45] Date of Patent: Feb. 28, 1995

[54] GUIDEWIRE TORQUE DEVICE FOR SINGLE-HAND MANIPULATION

[75] Inventor: Michael J. Horzewski, San Jose, Calif.

[73] Assignee: B. Braun Medical, Inc., Bethlehem, Pa.

[21] Appl. No.: 105,816

[22] Filed: Aug. 11, 1993

[51] Int. Cl.⁶ .............................................. A61B 5/00
[52] U.S. Cl. .................................................. 128/657
[58] Field of Search .................. 128/457, 772; 604/95, 604/159, 171; 279/42, 48

[56] References Cited

U.S. PATENT DOCUMENTS

| | | | |
|---|---|---|---|
| 4,726,369 | 2/1988 | Mar | 128/303 |
| 4,957,117 | 9/1990 | Wysham | 604/95 |
| 5,137,288 | 8/1992 | Starkey et al. | 279/42 |
| 5,137,517 | 8/1992 | Loney et al. | 604/159 |
| 5,161,534 | 11/1992 | Berthiaume | 128/657 |
| 5,219,332 | 6/1993 | Nelson et al. | 128/657 |

FOREIGN PATENT DOCUMENTS 0534747  3/1993  European Pat. Off. ............ 128/772

*Primary Examiner*—Max Hindenburg
*Attorney, Agent, or Firm*—Townsend and Townsend Khourie and Crew

[57] ABSTRACT

A torque device capable of both securement to a guidewire and release with only one hand, is constructed of a pair of tubular elements, one terminating in a series of prongs with outer surfaces which form an outwardly expanding cone, and the other surrounding the prongs and containing an internal, inwardly extending flange which engages the outer surfaces of the prongs. When the tubular elements are slid apart relative to each other, the flange travels along the expanding outer surfaces of the prongs, forcing the prongs toward each other so that the prong tips grip the guidewire. Release is achieved by sliding the tubular elements back to a closed configuration.

7 Claims, 3 Drawing Sheets

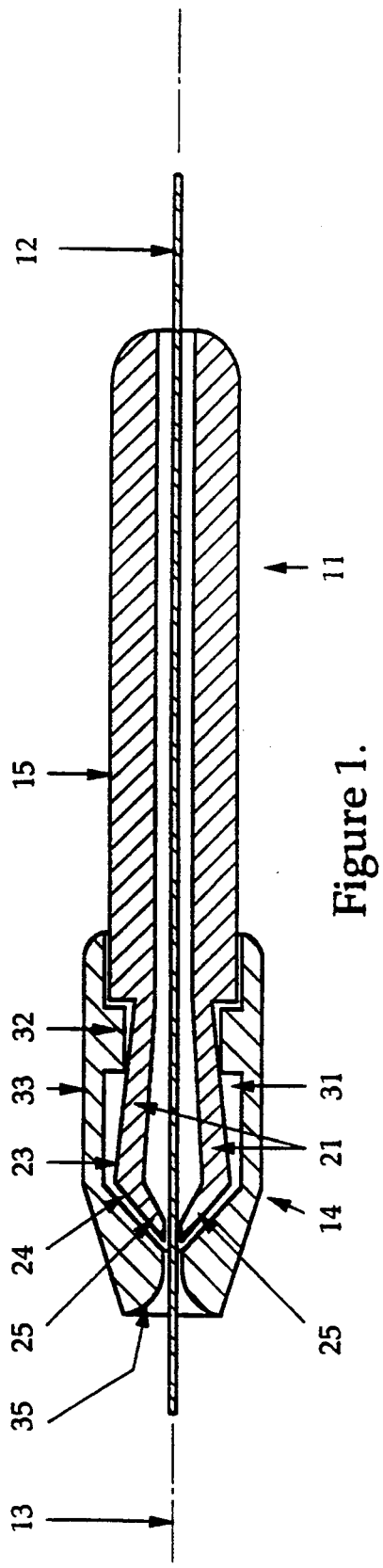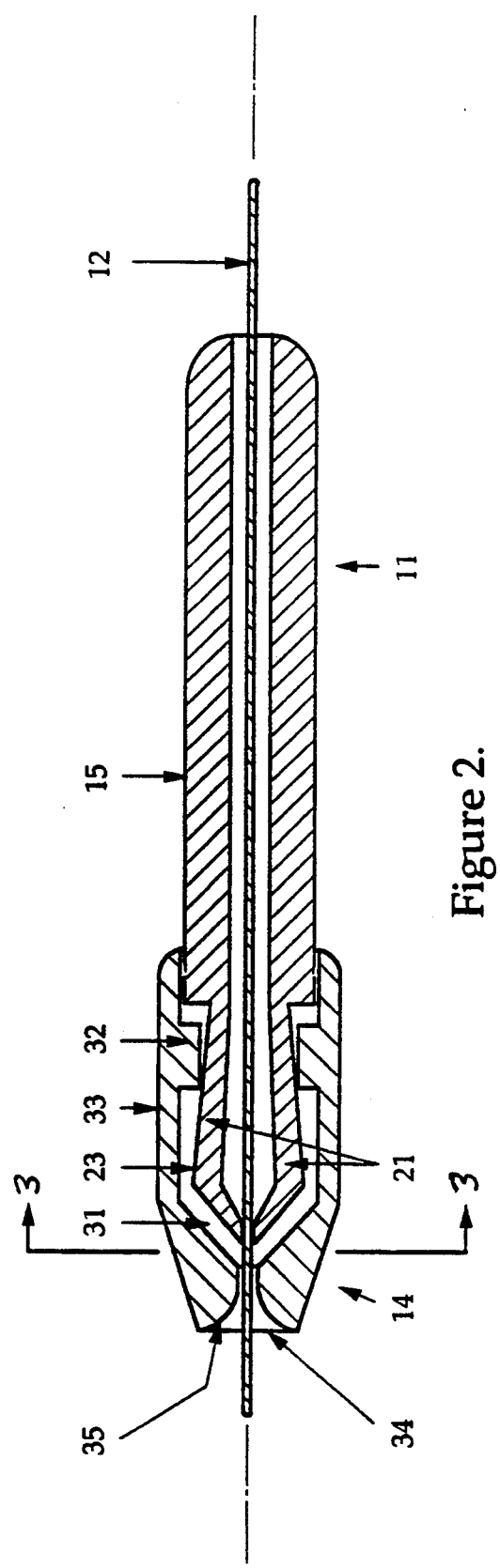

A - A

GUIDEWIRE TORQUE DEVICE FOR SINGLE-HAND MANIPULATION

This invention resides in the field of medical devices in general, and relates in particular to the guidewires used in conjunction with catheters used in intravascular and similar procedures. This invention is specifically concerned with methods and devices for the manipulation of a guidewire through branched or convoluted bodily passages such as a vasculature.

BACKGROUND OF THE INVENTION

For convenience, this invention will be described in the context of an angioplasty procedure as a prime example of the use of guidewires.

The guidewire is relied upon for the proper placement of an angioplasty catheter at the region of a stenosis. With its slightly bent distal tip, the guidewire can be steered into the appropriate arterial branches by manual rotation of the guidewire at its proximal end while the guidewire is advanced.

Manipulation of the guidewire in this manner requires a device known as a "gripping device," "steering device" or "torque device" since the wire itself is of a very small diameter. The torque device, which is secured to the distal end of the guidewire, is large enough to be comfortably and securely gripped by the user's hand. The device, which is generally cylindrical in shape and has a knurled outer surface for easy handling, grips the guidewire in a manner which is secure and yet readily releasable so that the device can be slid back along the guidewire to permit further advancement of the guidewire.

Currently used torque devices require two hands for both tightening and releasing, one hand to grip the body of the device and the other to tighten or loosen the gripping mechanism inside the device. Since one hand is generally used to hold the catheter, the user who is advancing the guidewire through the vasculature must release his hold on the catheter each time the torque device is to be repositioned on the guidewire. Since the the device is typically repositioning on the guidewire for every advancement of 2–3 centimeters of the length of the guidewire, these devices can detract from the efficiency of a procedure where economy of time is critical to the survival of the patient. Devices which can be operated with one hand are known in the literature, but these are structurally inferior since they lack the ability to strongly grip the guidewire.

SUMMARY OF THE INVENTION

These and other disadvantages are overcome by the present invention, which resides in a guidewire gripping device formed from a pair of tubular members, one of which terminates at one end in a multitude of prongs and the other fitting over the prongs in a manner permitting it to slide relative to the prongs and to the first tubular member in the axial direction. The tubular members are hollow to permit passage of the guidewire, and the tips of the prongs encircle the central axis of the device, likewise to permit passage of the guidewire. The prongs are shaped such that their tips are far enough apart to permit unimpeded axial movement of the device over the guidewire, but the prongs are of a resilient construction, permitting them to be bent or compressed toward each other to grip the guidewire on all sides. A circular protrusion or ring on the interior of the second tubular member extending inward contacts the sloping outer surfaces of the prongs such that when the second tubular member is slid over the prongs with the ring moving toward the prong tips, the ring compresses the prongs, causing the tips to close over and grip the guidewire.

The two tubular members are readily moved relative to each other with a single hand, leaving the user's other hand free for controlling and stabilizing the catheter, and the tips of the prong provide a firm grip on the guidewire when the two tubular members are extended relative to each other. These and other advantages of the device will become apparent from the description which follows.

BRIEF DESCRIPTION OF THE DRAWINGS

FIG. 1 is a side view in cross section of a torque device illustrating the present invention, in combination with a guidewire. The cross section is taken parallel to the central axis of the device. The device is shown in a relaxed position in this drawing, with the guidewire not engaged by the device.

FIG. 2 is a side view in cross section of the torque device of FIG. 1, this time clamped over the guidewire.

DETAILED DESCRIPTION OF THE INVENTION AND PREFERRED EMBODIMENTS

Throughout this specification and the appended claims, the terms "distal" and "proximal" are used to designate the relative ends of components, sections or parts of the torque device of the present invention, of the guidewire with which it is used or a catheter used in conjunction with the guidewire. These terms are used in the sense in which they are widely used and well recognized among those knowledgable in the field of medical catheters. The "distal" end of any of these components, sections or pans refers to the end furthest inside or facing the vasculature when in use and furthest away from the physician or medical technician operating the catheter, whereas the "proximal" end refers to the opposite end, i.e., the end closest to the operator.

Figure 3:
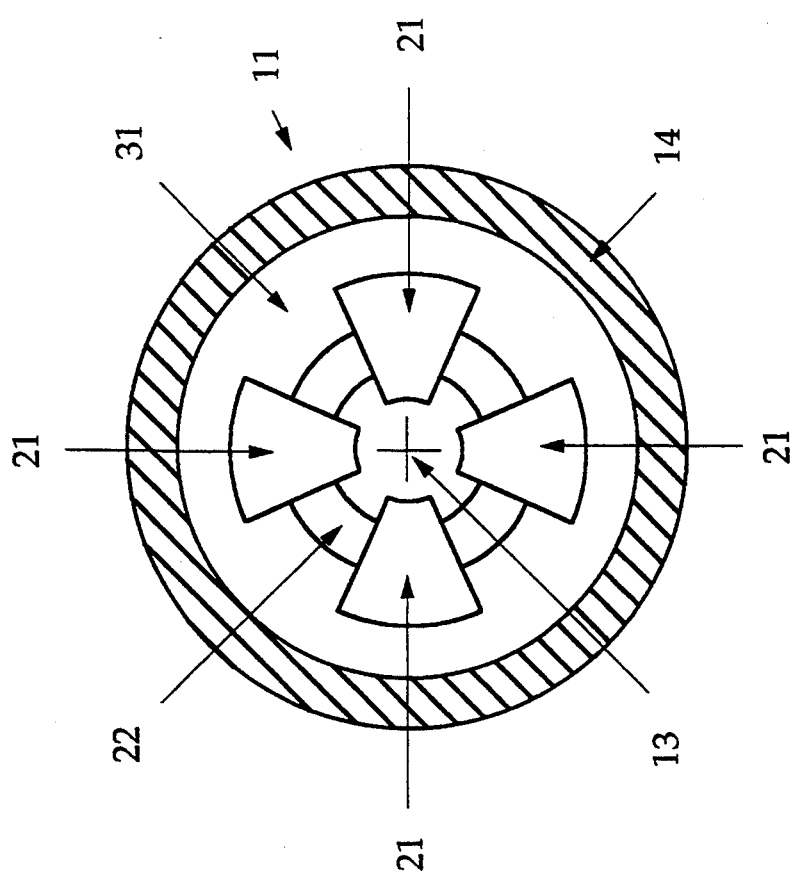
FIG. 3 is a further cross section view of the device of FIGS. 1 and 2, taken along the line 3—3 of FIG. 2 and enlarged relative to FIGS. 1 and 2, with the prongs slightly parted for clarity. This cross section is transverse to the central axis of the device.

For a thorough understanding of the invention as a whole, a single embodiment containing all of the features of the invention will be described in detail. This embodiment is depicted in FIGS. 1, 2 and 3.

FIGS. 1 and 2 depict a torque device 11 and a guidewire 12 passing through the torque device. From its exterior, the torque device 11, including both of its components, is a body of revolution about a central axis 13 which is approximately coincident with the guidewire 12. The device is constructed of two tubular elements 14, 15, each of which has a central axis which coincides with the common central axis 13 of the device as a whole. While the device can be oriented in either direction when in use, for the purposes of this description it is assumed that the direction to the left of FIGS. 1 and 2 is the distal direction, and the direction to the right is the proximal direction. Thus, the leftmost tubular element 14 may be referred to as the distal tubular element, and the rightmost 15 as the proximal tubular element.

The proximal tubular element 15 terminates at its distal end in a series of prongs 21. At least three prongs are included, preferably four, as shown in FIG. 3. The prongs are separated from each other by longitudinal slots 22 cut into the proximal tubular element and opening at the distal end of the element. The prongs each have an outer contour which includes a sloping segment 23 which slopes away from the central axis in the distal direction, thereby forming an outwardly expanding cone in the distal direction, and a tapering segment 24 distal to the sloping segment. Each tapering segment 23 ends in a tip 25, which is the portion of the prong closest to the central axis 13 of the device. The tips of the prongs are evenly spaced around the central axis 13 of the device, such that when the prongs are bent inward the tips contact the guidewire and the guidewire is gripped by the tips on all sides with equal pressure.

While the proximal tubular element 15 and the prongs 21 are shown in the drawings as a single unit of unitary construction, they may also be separate pieces joined together in a rigid fashion, such as by a press fit, by bonding, or by a threaded connection. This would be useful when the prongs are constructed of a different (for example, heavier) material than the tubular member itself.

The distal tubular element 14 has a central cavity 31 which receives the prongs. Formed along the inner wall of the central cavity 31 is an inwardly protruding flange 32 which extends around the full circumference of the inner wall. The flange 32 engages the sloping segments 23 of all of the prongs 21. When the distal tubular element is manually slid from the position shown in FIG. 1 to that shown in FIG. 2, the flange 32 travels along the length of the outwardly expanding segments 23 from their narrow proximal ends toward their wider distal ends. The width of the flange 32 is such that it remains in contact with the outwardly expanding segments at all points along its path of travel. Travel of the flange in the distal direction thus causes the prongs 21 to be bent or compressed toward each other, narrowing the gap between the prong tips 25, and ultimately forcing the prong tips 25 against the guidewire, thereby securing the device to the guidewire 12. Simple manual manipulation of the distal tubular element 14 in this manner will provide sufficient gripping force to secure the device and guidewire together in immovable engagement until the distal tubular element 14 is manually returned to the position shown in FIG. 1. To achieve this effect, the prongs 21 are of sufficient rigidity and resiliency to both create a strong grip on the guidewire and to return immediately to the relaxed configuration of FIG. 1 upon release. The expanding cone formed by the outwardly sloping segments 23 of the prongs, when relaxed as shown in FIG. 1 forms an angle relative to the central axis 13 of from about 2 degrees to about 10 degrees.

Manipulation of the device with one hand is readily achieved, for example, by wrapping one's third, fourth and fifth fingers around the proximal tubular element 15 and securing that element against the palm of the hand, while holding the distal tubular element 14 with the thumb and forefinger, which can move the distal element relative to the proximal element the short distance between the clamping and release positions. To facilitate the gripping of the device, the outer surface 33 of the distal tubular element may be knurled, specially contoured, or otherwise modified from a simple cylindrical surface.

The distal end of the distal tubular element 14 has an axial port 34 for passage of the guidewire. The outer surface 35 of the port is flared outward with a convex cross section on each side of the opening. This facilitates the insertion of the guidewire into the device, or the placement of the device over the guidewire.

As an additional feature contained in certain embodiments of the basic concept of this invention, the two tubular elements may be constructed of a material which glows in the dark, such as a resin which incorporates a phosphorescent pigment. An example of such a pigment is a mixture of zinc sulfide and zinc oxide, which will luminesce green.

Figure 4:
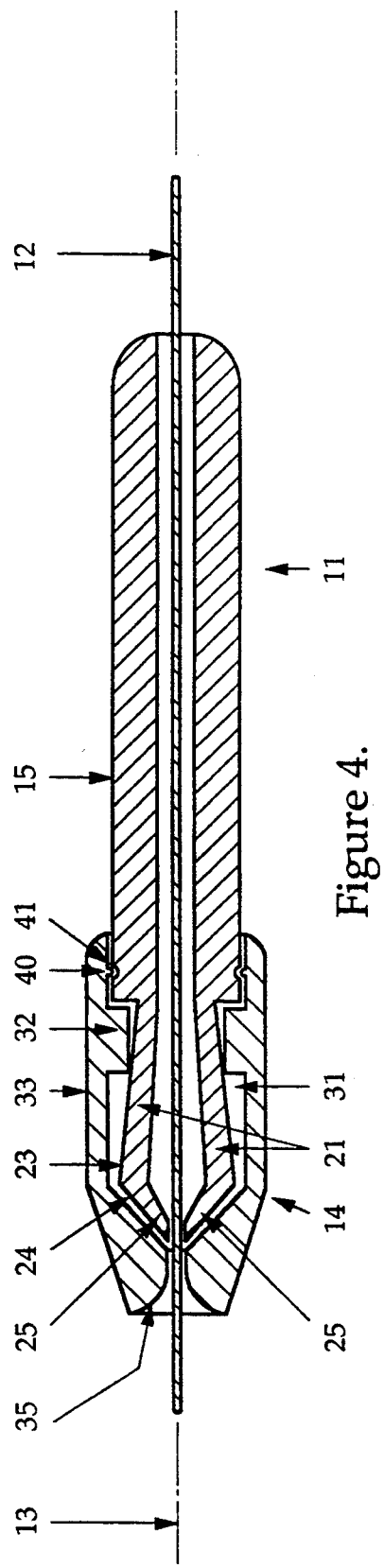
FIGS. 4 and 5 illustrate a variation of the torque device of FIG. 1, shown in side view cross section, differing from the FIG. 1 device by the inclusion of a releasable locking mechanism. The locking members are engaged in FIG. 4 and disengaged in FIG. 5.
Figure 5:
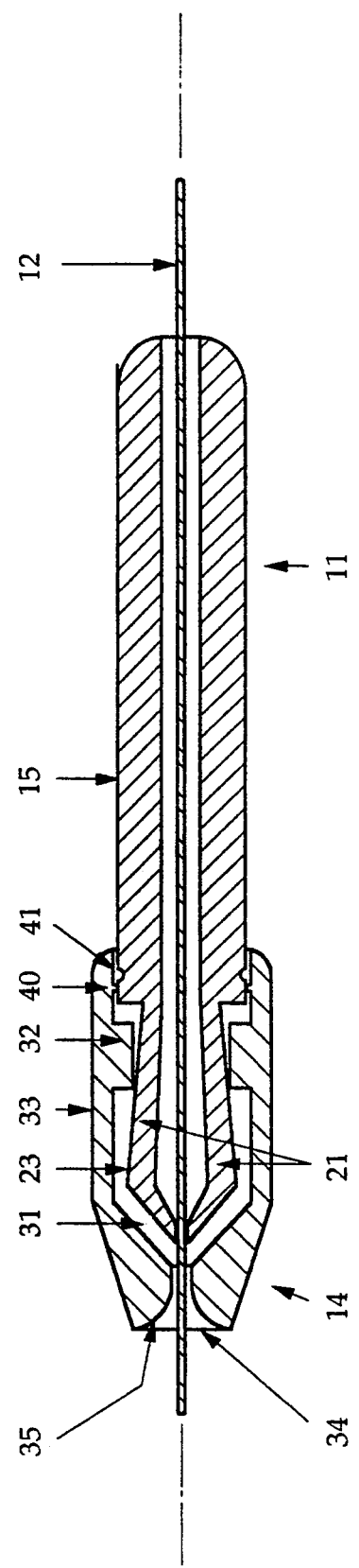

A feature of certain additional embodiments of the basic concept of this invention is a releasable locking mechanism to fix the two tubular members relative to each other. One example of such a mechanism is shown in FIGS. 4 and 5. Here the distal tubular element 14 has a protrusion 40 which mates with an indentation 41 in the facing surface of the proximal tubular element 15. Since the materials of construction are resilient, the protrusion and indentation will snap into engagement, and the engagement will be maintained until the tubular elements are pulled apart with a small exertion of manual force by the operator. The protrusion 40 may be a ring-shaped flange which extends around the entire circumference of the inner surface of the distal tubular element 14, and the indentation 41 likewise a groove which extends around the entire circumference of the outer surface of the proximal tubular element 15. Alternatively, the protrusion 40 may be a single knob or a series of knobs spaced around the circumference, and the indentation 41 may be an individual depression for each knobs, or a circumferential groove for all of the knobs. In other alternatives, the protrusion and indentation may be positioned such that they are in engagement when the tubular elements are in the extended or elongated position of FIG. 5, rather than when the tubular elements are in the relaxed position of FIG. 4 as shown. Still further, the protrusion and indentation may be reversed, with the protrusion on the outer surface of the proximal tubular element 15 and the indentation in the inner surface of the distal tubular element 14. A still further alternative which does not involve protrusions and indentations would be a screw clamp to force the two tubular elements against each other in a friction engagement. Still further alternatives will be readily apparent to those skilled in the art.

The dimensions of the device and the materials of construction are not critical and may vary. In a presently preferred embodiment having the form shown in the drawings, the distal tubular element 14 is approximately 1 inch (2.54 cm) in length, with a diameter of about 0.38 inch (0.97 cm), and the proximal tubular element 15, including the prongs 21, is approximately 3.5 inches (8.9 cm) in length with a diameter of 0.30 inch (0.76 cm). The angle of the sloping segments 23 relative to the central axis 13, when the prongs are relaxed, is about 5 degrees, and the range of movement of the distal tubular element relative to the proximal tubular element for securing and releasing the guidewire is a distance of from about 0.100 inch to about 0.250 inch (0.25–0.64 cm). The materials used in this embodiment are brass, stainless steel or plastic. High modulus plastic is particularly useful for the prongs. The proximal tubular element 15 when made of plastic can be any suitable plastic, such as polyethylene, polypropylene, or similar materials.

The foregoing is offered primarily for purposes of illustration. It will be readily apparent to those skilled in the art that the configuration, dimensions, materials, orientation and other parameters of the device may be further modified or substituted in various ways without departing from the spirit and scope of the invention.

What is claimed is:

1. A device for gripping a catheter guidewire, said device comprising:

a first tubular member having first and second ends and a central axis and terminating at said first end in at least three resilient prongs arranged at equal intervals around said central axis, said resilient prongs having outer contours which include sloping surfaces which slope away from said central axis in the direction leading to said first end;

a second tubular member for receiving said resilient prongs and axially slidable thereover; and means for engaging said sloping surfaces of all of said resilient prongs simultaneously, and for compressing said resilient prongs toward each other when said second tubular member is slid relative to said first tubular member such that said means for engaging travels toward said first end.

2. A device in accordance with claim 1 in which said first tubular member terminates distally in four said resilient prongs.

3. A device in accordance with claim 1 in which said first end of said first tubular member is a distal end and said second end a proximal end, said second tubular member having correspondingly distal and proximal ends and opening at the distal end thereof in a flared port.

4. A device in accordance with claim 1 further comprising means for releasably locking said first and second tubular members relative to each other.

5. A device in accordance with claim 1 in which said sloping surfaces form an angle of from about 2 degrees to about 10 degrees relative to said central axis.

6. A device in accordance with claim 1 in which said means for engaging said sloping surfaces is a flange mounted to the interior of said second tubular member and extending inwardly.

7. A device in accordance with claim 1 in which said first tubular member, said second tubular member or both are formed of a material which includes a phosphorescent pigment.

* * * * *